US00PP12439P2

(12) United States Plant Patent
Krome et al.

(10) Patent No.: US PP12,439 P2
(45) Date of Patent: Mar. 5, 2002

(54) AVOCADO TREE NAMED 'ALPHA KROME'

(76) Inventors: William Henry Krome, deceased, late of Mami, FL (US); by Phoebe von P. Krome, legal representative, P.O. Box 900596, Homestead, FL (US) 33090; Neal Palmer Brooks, 17171 SW. 266th Ter., Homestead, FL (US) 33031

( * ) Notice: Subject to any disclaimer, the term of this patent is extended or adjusted under 35 U.S.C. 154(b) by 0 days.

(21) Appl. No.: 09/383,844

(22) Filed: Aug. 26, 1999

(51) Int. Cl.[7] ..... A01H 5/00
(52) U.S. Cl. ..... Plt./200

(58) Field of Search ..... Plt./200

*Primary Examiner*—Bruce R. Campell
*Assistant Examiner*—A Para
(74) *Attorney, Agent, or Firm*—Akerman, Senterfitt & Eidson, P.A.; Michael C. Cesarano

(57) ABSTRACT

A new variety of avocado is distinguished by its late maturing fruit. The tree blooms in April and the blooms are of the A type, flowering in the afternoon. The fruit matures and can be picked in March of the following year. The fruit is an ovate berry that has a thick hard shelled expcarp, which is pebbly textured, dark green, weighs between 15 and 20 ounces and averages 3.5 inches in diameter.

7 Drawing Sheets

BACKGROUND OF THE INVENTION

The standard growing season for avacados in Florida is from mid-summer through mid-winter. Following the harvesting of avocados in January and February, fresh avocado fruit is scarce and must be imported from other growing areas. However, the popularity of avocados is constant throughout the year, and there is a demand for avocados during the months in which Florida avocados are generally not available. The variety of avocado described and claimed herein matures in March, when there are no other Florida varieties in production. This avocado is noteworthy because of the lateness of the maturity of the fruit.

BRIEF SUMMARY OF THE INVENTION

All color descriptions employ the Munsell Color Charts for Plant Tissues, Macbeth Division of Kollmorgen Instruments Corp., 405 Little Britain Rd., New Windsor, N.Y. 12553. The complete Munsell notation for any chromatic color is written: Hue (Value/Chroma).

The name of this new and distinct variety of avocado plant is 'Alpha Krome' Avocado tree. The botanical name of the observed plant is *Persea americana* Miller.

This tree was first observed in a thirty acre avocado grove located at 10695 S.W. 207$^{th}$ Avenue, in Homestead, Fla. in March 1999. The tree is estimated to be between 25 and 30 years of age, and is growing in an avocado field that has been in production since 1956. It was noted that the tree had fruit on it at a time when other avocado varieties were bare of fruit. The parentage of this variety is unknown, but it differs from similar varieties of avocado because of the lateness of the maturity of the fruit. Two hundred fifty cuttings were taken from the instant tree and grafted on to seedling rootstock in the late spring, 2000.

The new avocado variety seems to express more resistance than other late varieties do to *Cercospora purpruea* and *Colletotrichum gloeosporoides* pathogens. This variety's tolerance to drought or frost is not known. The fruit is sensitive to chilling injury in storage and should be stored at or above 52 degrees F. At this time, it is not possible to adequately describe plant vigor except to state that the vigor of this tree is similar in height, spread and growth habit with other avocado trees of similar age in the grove in which it is located.

DETAILED BOTANICAL DESCRIPTION

Figure 1:
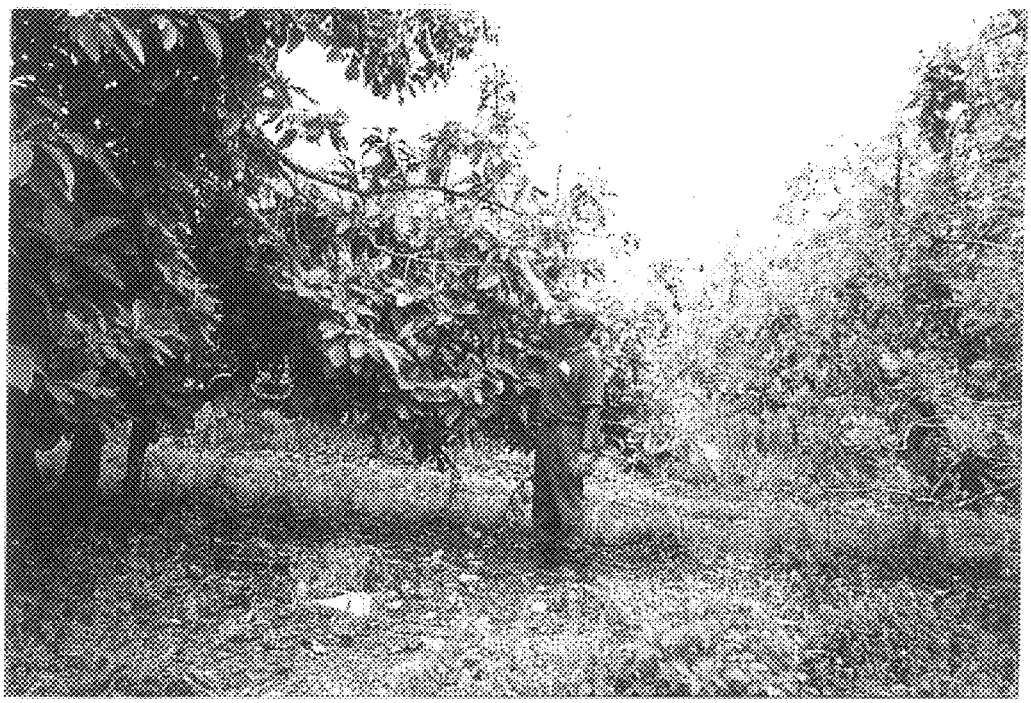
FIG. 1 shows a lower portion of the avocado tree with limbs bearing fruit.
Figure 2:
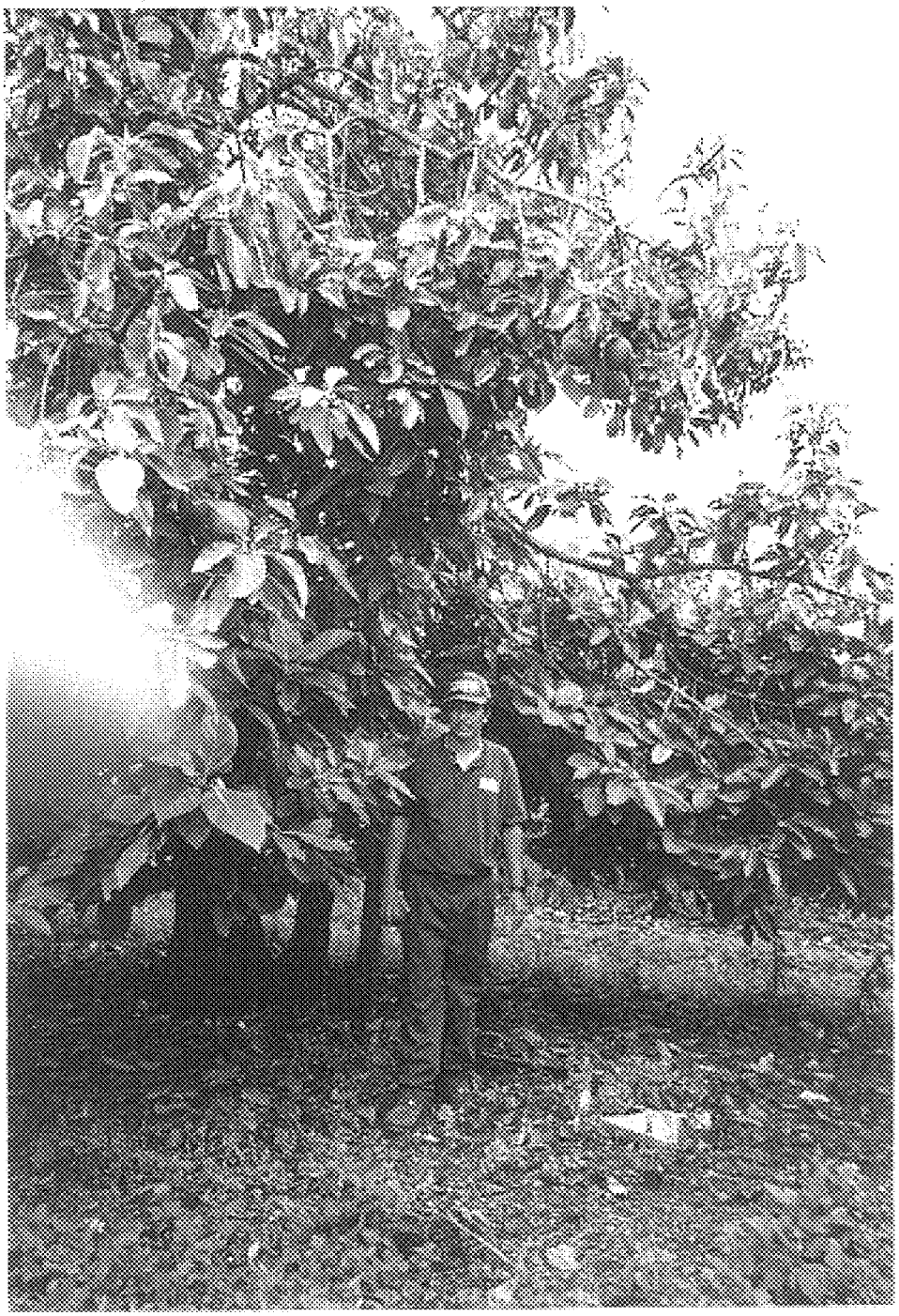
FIG. 2 shows the scale of a lower quadrant of the avocado tree with a man standing next to the tree.
Figure 3:
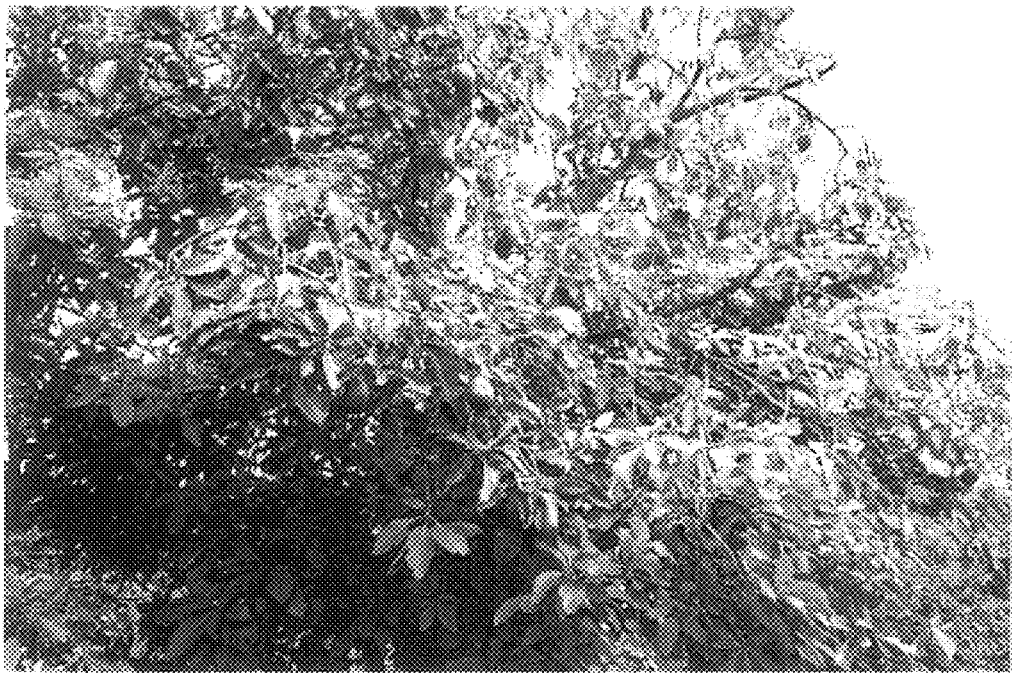
FIG. 3 shows the upper portion of the avocado tree.

The tree is a vigorous upright growing tree, 30 feet high with a spread of 15 feet, as is shown in FIGS. 1–3. The diameter of the main trunk is 24 inches, and splits into four 8 inch vertical sub-trunks 4 feet above the ground. Pendant branches 4 inches in diameter split off of the vertical sub-trunks, these in turn giving way to smaller and smaller branches growing in pendant fashion. One year of wood averages one inch in diameter.

The bark on the trunk, sub-trunks, and branches is light in color 2.5 Y (7/2). One year old wood is somewhat darker at 7.5 YR (4/2). New shoots average ½ inches in diameter and are greenish yellow 5Y (7/8).

The foliage is of average density and leaves are large and dark green, as appears in FIGS. 1 and 2. The leaves are alternate, entire and pinnately veined. They are elliptic, narrowly acute at the apex and acute at the base. The leaves are 4 to 16 inches in length, pubescent when young, becoming smooth and leathery when mature. The upper surface of the leaf exhibits a range of dark green from 7.5 GY (3/4 to 4/4). The underside of the leaf ranges from 5 GY (5/4 to 6/4). Leaf veins are a greenish yellow color of 2.5 GY (7/8), and the petioles are 2.5 GY (7/6). The leaves are not fragrant when crushed.

Multiple flowers on axillary panicles are borne in a pseudoterminal position and the central axis of the inflorescence terminates in a shoot. Flowers are perfect, with 12 stamens, 9 of which are functional, each having 4 pollen chambers. The single pistil has one carpel with one ovule. The flowers are ⅜ to ½ inch in diameter. They lack petals but have 2 whorls of 3 perianth lobes, and are pubescent. The color of the lobes and the pistil is light green 2.5 GY (8/4), the sepals are darker at 2.5 GY (7/6), and the anthers are yellow 2.5 Y (8/10). The flowers are not fragrant. The tree blooms in April and the blooms are of the A type. Fruit matures and can be picked in March of the following year.

Figure 4:
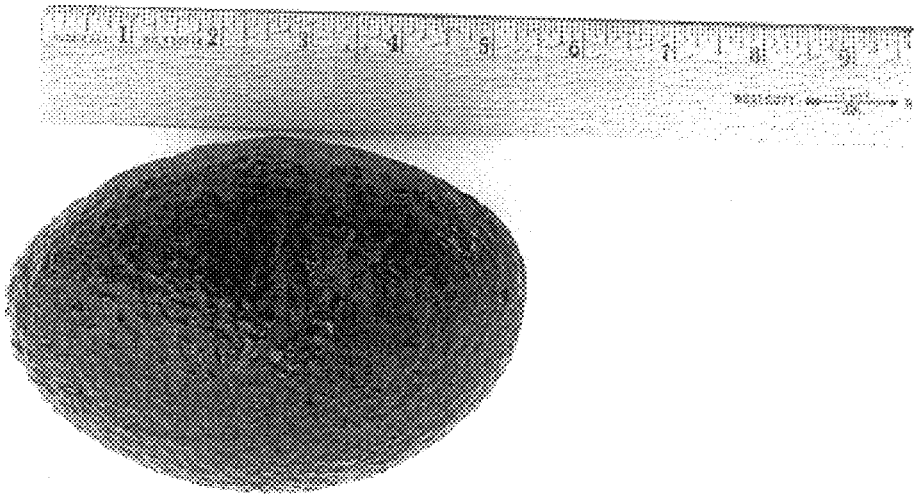
FIG. 4 shows the scale in inches of a typical fruit of the tree measured against a ruler.
Figure 5:
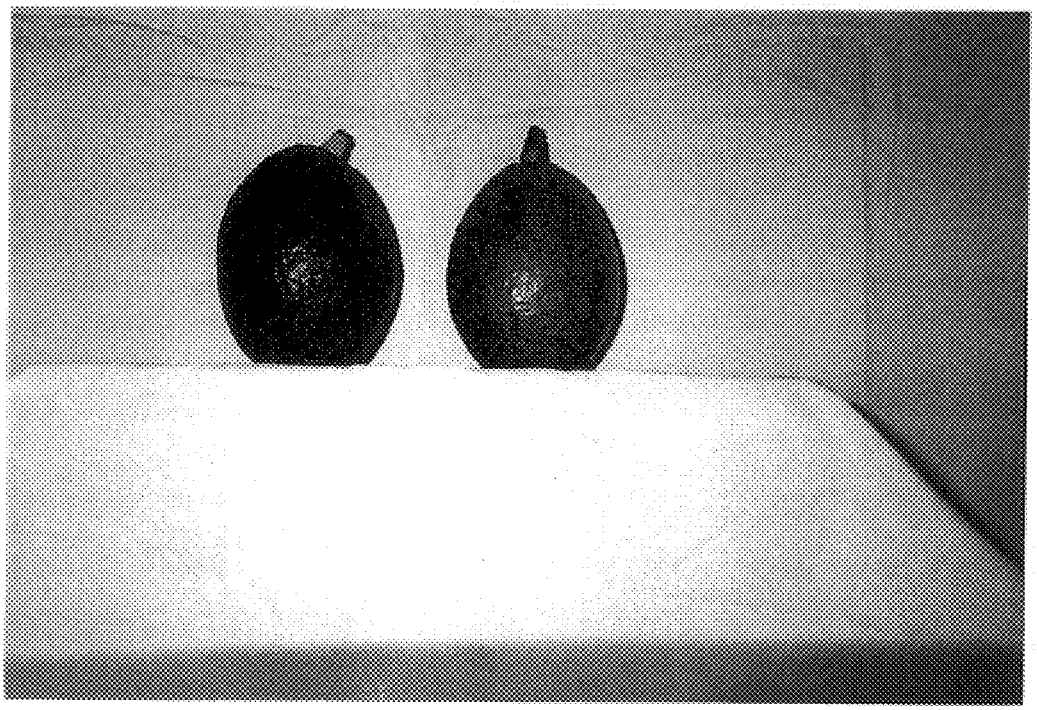
FIG. 5 shows the external color and surface of two avocados from the tree.

FIG. 5 shows the outside of the fruit, which is an ovate berry that matures in March. It has a thick (1/16 inch) hard shelled exocarp, which is pebbly textured, and dark green 5 GY (4/6). The fruit weighs between 15 and 20 ounces and averages 3.5 inches in diameter, as shown in FIG. 4.

Figure 6:
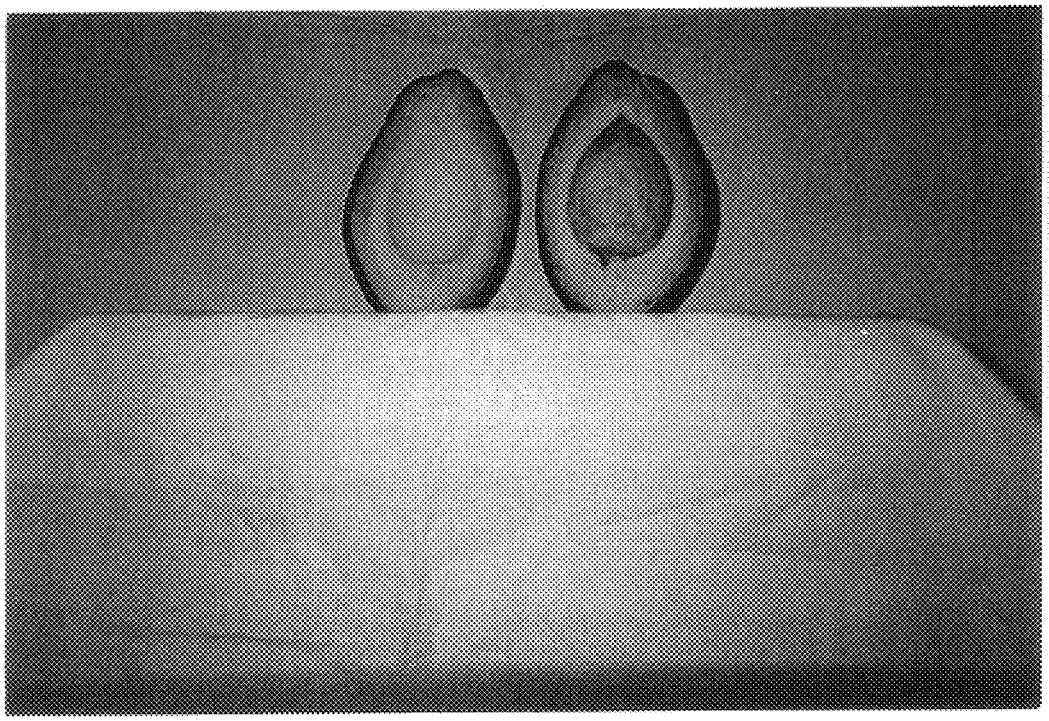
FIG. 6 shows the color and internal configuration of the fruit of the avocado tree.
Figure 7:
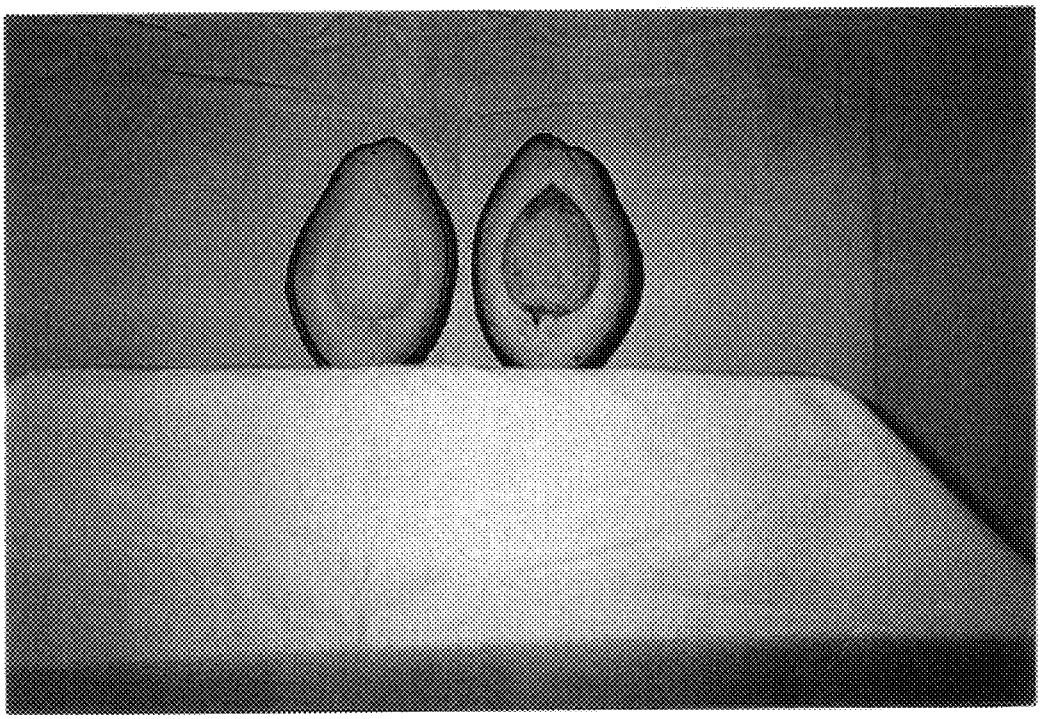
FIG. 7 shows the color and internal configuration of the fruit of FIG. 6 under marginally different lighting conditions.

In FIGS. 6 and 7, the interior of the fruit is seen to have a mesocarp color that is green near the shell 5GY (7/8) and yellow near the seed cavity 5Y (8/10). Lenticels are numerous (100–200 per square inch) on the fruit and are light yellowish green in color 2.5 GY (7/10). The fruit also has an excellent flavor.

The seed (not shown) is tight in the cavity, oblate, and is 2½ to 3 inches long and is covered by a dark brown endocarp 5 YR (4/4). The Cotyledons are textured and light brown in color 5 YR (6/8).

We claim:

1. A new and distinct variety of avocado tree substantially as described and illustrated and characterized as to novelty by its maturing very late in the season.

* * * * *